(12) United States Patent
Gerdes et al.

(10) Patent No.: US 12,163,175 B2
(45) Date of Patent: *Dec. 10, 2024

(54) SYSTEMS AND METHODS FOR CO-CULTURE OF OXYGEN SENSITIVE BACTERIA AND YEAST

(71) Applicant: POET RESEARCH, Inc., Sioux Falls, SD (US)

(72) Inventors: Benjamin M. Gerdes, Yankton, SD (US); Kyle R. Larson, Yankton, SD (US)

(73) Assignee: POET Research, Inc., Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 18/217,828

(22) Filed: Jul. 3, 2023

(65) Prior Publication Data

US 2024/0043881 A1 Feb. 8, 2024

Related U.S. Application Data

(63) Continuation of application No. 17/198,099, filed on Mar. 10, 2021, now Pat. No. 11,732,278.

(60) Provisional application No. 63/074,133, filed on Sep. 3, 2020, provisional application No. 62/988,050, filed on Mar. 11, 2020.

(51) Int. Cl.
*C12P 7/06* (2006.01)
*C12P 1/02* (2006.01)
*C12P 1/04* (2006.01)

(52) U.S. Cl.
CPC .............. *C12P 7/06* (2013.01); *C12P 1/02* (2013.01); *C12P 1/04* (2013.01)

(58) Field of Classification Search
CPC ............... C12P 7/14; C12P 7/08; C12P 7/06
See application file for complete search history.

(56) References Cited

U.S. PATENT DOCUMENTS 8,759,069 B2  6/2014 Fox et al.
11,732,278 B1* 8/2023 Gerdes .................... C12P 7/14
                                                435/161
2010/0093050 A1  4/2010 Hakalehto et al.
2019/0323041 A1 10/2019 Rasmussen et al.

FOREIGN PATENT DOCUMENTS

CN  102160595      12/2012
CN  103609985      10/2013
CN  106520584      10/2019
JP  H0888572        1/1996
WO  WO 2010096673   8/2010
WO  WO 2013090053  12/2012
WO  WO 2020100072  11/2019

OTHER PUBLICATIONS

Abate (1996) "Ethanol production by a mixed culture of flocculent strains of *Zymomonas mobilis* and *Saccharomyces* sp." Appl Microbiol Biotechnol 45:580-583.
Agrawal (1994) "Fermentation of paddy malt mash to ethanol by mixed cultures of *Saccharomyces cerevisiae* and *Zymomonas mobilis* ZM4 with Penicillin G" J of Fermentation and Bioengineering 77(2):218-220.
Amin (1983) "Determination of by-products formed during the ethanolic fermentation using batch and immobilized cell systems of *Zymomonas mobilis* and *Saccharomyces bayanus*" Eur J Appl Microbiol Biotechnol 18:1-5.
Chen (2011) "Development and application of co-culture for ethanol production by co-fermentation of glucose and xylose: a systematic review" Journal of Industrial Microbiology & Biotechnology 38:581-597.
Davidson and Stephanopoulos (1986) "Effect of pH oscillations on a competing mixed culture" Biotechnology and Bioengineering 28(8):1127-1137.
Faria-Oliveira et al. (2015) "The Role of Yeast and Lactic Acid Bacteria in the Production of Fermented Beverages in South America".
Finn (2014) "Understanding bacterial adaptation to aerobic and anaerobic environments through experimental evolution and whole genome analysis: a thesis presented in fulfilment of the requirements for the degree of Doctor of Philosophy in Genetics at Massey University, Palmerston North, New Zealand".
Goers et al. (2014) "Co-Culture Systems and Technologies Taking Synthetic Biology to the Next Level" Journal of the Royal Society 11:20140065.
Hanly and Henson (2013) "Dynamic metabolic modeling of a microaerobic yeast co-culture: predicting and optimizing ethanol production from glucose/xylose mixtures" Biotechnology for Biofuels 6:44.
Kato et al. (1997) "Anaerobe Tolerance to Oxygen and the Potentials of Anaerobic and Aerobic Cocultures for Wastewater Treatment" Braz. J. Chem. Eng. 14(4).
Moscoviz et al. (2021) "Directing carbohydrates toward ethanol using mesophilic microbial communities" Current Opinion in Biotechnology 67:175-183.
Park et al. (2012) "One-pot bioethanol production from cellulose by co-culture of *Acremonium cellulolyticus* and *Saccharomyces cerevisiae*" Biotechnology for Biofuels 5:64.
Raman et al. (2008) "Screening of Zymomonas Mobilis and *Saccharomyces cerevisiae* strains for ethanol production from cassava waste" Rasayan J. Chem. 1(3):537-541.
Stephens and Lyberatos (1987) "Effect of cycling on final mixed culture fate" Biotechnology and Bioengineering 29(6):672-678.
Zuroff et al. (2013) "Consortia-mediated bioprocessing of cellulose to ethanol with a symbiotic Clostridium phytofermentans/yeast co-culture" Biotechnology for Biofuels 6: 59.

* cited by examiner

*Primary Examiner* — Tekchand Saidha
(74) *Attorney, Agent, or Firm* — FisherBroyles, LLP; Cara L. Crowley-Weber; Cary Reeves

(57) ABSTRACT

Methods, compositions, and systems for propagation and fermentation of co-cultures of an oxygen sensitive bacteria and a yeast, particularly large scale operations for production of a bioproduct are provided. Methods of co-culture provide growth sufficient to minimize growth of contaminating bacteria.

36 Claims, 1 Drawing Sheet

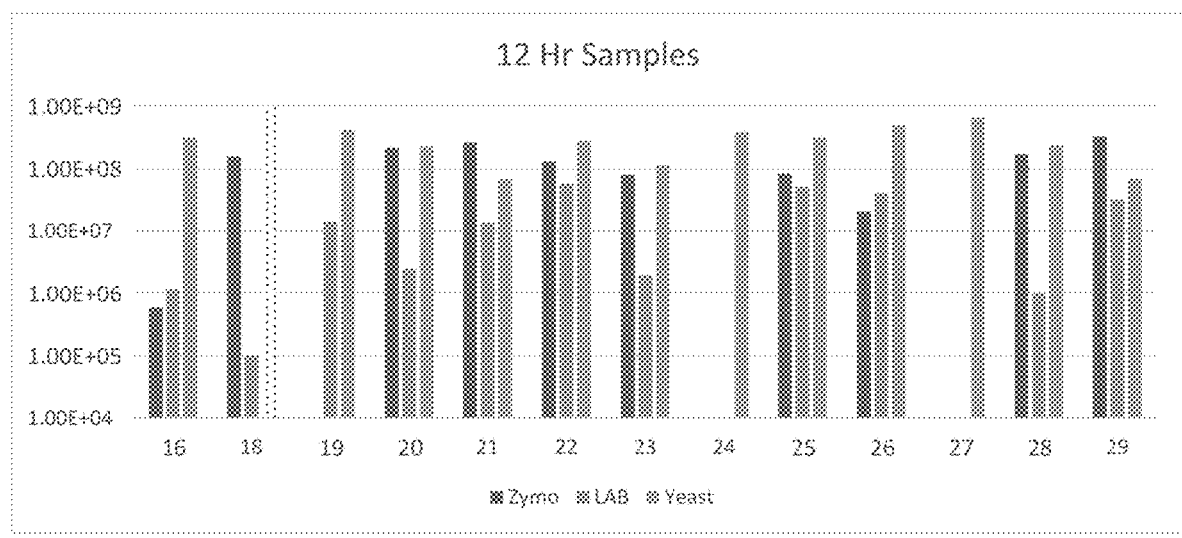

SYSTEMS AND METHODS FOR CO-CULTURE OF OXYGEN SENSITIVE BACTERIA AND YEAST

RELATED APPLICATIONS

This application is a continuation application of U.S. application Ser. No. 17/198,099 titled "Systems and Methods for Co-Culture of Oxygen Sensitive Bacteria and Yeast" filed Mar. 10, 2021, which claims the benefit of U.S. Provisional Application No. 62/988,050 titled "Systems, Compositions, and Methods of Fermentation with *Z. Mobilis*" filed Mar. 11, 2020 and U.S. Provisional Application No. 63/074,133 titled "Systems and Methods for Co-Culture of Aeration Sensitive Bacteria and Yeast" filed Sep. 3, 2020 all of which are incorporated herein by reference.

TECHNICAL FIELD

Provided herein are methods, compositions, and systems for propagation and fermentation in a biorefinery, for example, in large scale operations for production of ethanol and dried distiller's grain.

BACKGROUND OF THE INVENTION

Fermentation processes utilize cultured microorganisms to convert carbon sources to a target bioproduct such as various alcohols, pharmaceuticals, proteins, etc. Example carbon sources include starch obtained from grain-based feedstocks (e.g., corn, sorghum/milo, barley, wheat, etc.), sugar obtained from sugar crops (e.g., sugar cane, sugar beets, etc.) and carbohydrate containing streams from pulp, agriculture and food processing (e.g. spend liquors, residues, waste streams, etc.) among others. Enzymes, whether endogenous to the grain, added to the fermenter, or produced by the primary microorganism or an adjunctive microorganism, convert the carbon source into a simple sugar that may be utilized by the microorganism. For example, amylases can convert starch to glucose. The microorganism then converts the simple sugar to the target bioproduct. For example, yeast, acting simultaneously with the enzymes, convert glucose to ethanol and carbon dioxide in a typical corn-to-ethanol biorefinery.

In a conventional cooked process, slurried feedstock is cooked to liquefy starch in the feedstock. In a raw starch hydrolysis (RHS) process, the feedstock is not cooked and very high gravity (VHG) fermentation may be practiced in which a commercially available distiller's yeast is able to produce approximately 15 to 16 percent weight to volume ethanol (approximately 19 to 20.2 percent volume to volume ethanol).

A fermentation mash, whether in a cooked process or a RHS process, may become contaminated by bacteria that produce undesirable end-products. One substantial source for contaminant bacteria in a biorefinery, e.g. an ethanol production facility, is the feedstock. As much as 10,000 to 1,000,000 bacterial cells per gram enter the facility with the incoming grain. A majority of active contaminant bacteria belong to the classes of bacteria that can adapt and grow well in the biorefinery production conditions, e.g. lactic acid bacteria (LAB). Eventually, these contaminant lactic bacteria can become established in the production facility if proper measures for control are not taken.

Contaminant bacteria typically have a faster growth rate than the cultured microorganism, e.g. yeast, under ideal conditions. These bacteria, when they are in high numbers in the substrate, can begin to grow rapidly even before the cultured microorganism, e.g. yeast, is inoculated (added) to the mash. The contaminant bacteria can easily grow to levels that would produce enough end-products, e.g. including lactic and acetic acids, to slow down the efficiency of target bioproduct, e.g. ethanol, production by the cultured microorganism, e.g. yeast, ultimately leading to a loss in yield. The contaminant bacteria also consume carbon sources and other nutrients that would otherwise be converted to the target bioproduct by the cultured microorganism.

Many different microorganisms, including yeast and bacteria, may be cultured to produce a target bioproduct. *Saccharomyces cerevisiae* (*S. cerevisiae*) is widely used in producing various bioproducts, e.g., ethanol, butanol, pharmaceuticals, precursor chemicals, etc. Various bacteria have also been used or considered for culture including those that naturally produce the target bioproduct and those engineered to do so. Some examples include *Escherichia coli* (*E. coli*), lactic acid bacteria, e.g. *Lactobacillus casei* (*L. casei*), and *Zymomonas mobilis* (*Z. mobilis*) among others. The gram negative facultative anaerobic bacterium, *Z. mobilis* has been considered as a potential alternative to yeast for ethanol production. The use of *Z. mobilis* has advantages over yeast, including higher specific rate of sugar uptake, lower biomass production, and higher volumetric sugar uptake and ethanol productivity. A commonly known drawback of *Z. mobilis* is that it can tolerate only up to approximately 12 percent weight to volume ethanol (approximately 15.2 percent volume to volume) whereas yeast, e.g., can tolerate up to approximately 18 percent weight to volume (approximately 23 percent volume to volume).

A number of strategies, including the use of low pH (between pH of 4.2 to 4.5) in fermentation, minimal use of antibiotics, and good plant management practices are used to keep the levels of contaminant bacteria to a small quantity. However, natural "non-antibiotic" solutions that eliminate the effects caused by contaminant bacteria are desirable.

The present invention is directed toward overcoming one or more of the problems discussed above.

SUMMARY OF THE INVENTION

Provided herein are compositions, methods, and systems for propagation and fermentation, for example, fermentation used in the production of bioethanol.

Provided herein are compositions comprising a primary feedstock, one or more cultured microorganisms, e.g. a yeast such as *S. cerevisiae* and a bacteria such as *Z. mobilis*, and water. The primary feedstock comprises the sugar source for propagation and fermentation by the microorganisms.

Also provided herein are compositions comprising a primary feedstock, one or more cultured microorganisms, e.g. a yeast such as *S. cerevisiae* and a bacteria such as *Z. mobilis*, hop acids, and water. In some aspects, the hop acids are present in the composition in an amount of about 25 ppm to about 40 ppm.

Provided herein are methods of reducing contamination during ethanol production in the raw starch hydrolysis process by utilizing a cultured bacteria, e.g. *Z. mobilis*, as a "probiotic" inoculant to combat lactic acid bacterial infection and contamination. The methods comprise (a) combining a feedstock, a yeast, a cultured bacteria, e.g. *Z. mobilis*, and water in a propagator and/or fermenter; and (b) fermenting the feedstock according to conditions provided herein.

Provided herein are methods of reducing undesired bacterial contamination, such as wild-type lactic acid bacterial (LAB) contamination, in a fermentation. In some aspects, the method comprises inoculating a feedstock with a cultured bacteria, e.g. *Z. mobilis*, prior to introduction of yeast.

In some aspects, the method comprises inoculating the feedstock with yeast prior to the addition of a cultured bacteria, e.g. *Z. mobilis*.

In some aspects, the method comprises varying the oxygen levels in a fermenter. Oxygen levels in a fermenter can be adjusted in ways known in the art, for example, by injecting oxygen, injecting air (aeration), using diffusers, or adding oxidizing chemicals. In some aspects, stopping the injections/additions allows the oxygen to be consumed or dissipated and therefore diminished to an extent that the oxygen sensitive bacteria can grow. Oxygen levels can also be decreased by injecting non-oxygen gas to liberate oxygen, using oxygen scavenging chemicals, and/or applying oxygen absorbers.

In some aspects, the method comprises varying the aeration levels in a fermenter.

In some aspects, the method comprises varying the timing of oxygenating a fermenter. In some aspects, oxygenation is performed in the initial stages of fermentation. In some aspects, oxygenation is performed in the later stages of fermentation.

In some aspects, the method comprises varying the timing of the aeration in a fermenter. In some aspects, aeration is performed in the initial stages of fermentation. In some aspects, aeration is performed in the later stages of fermentation.

Provided herein are methods of ethanol fermentation. In some embodiments, the method comprises (a) inoculating a feedstock with *S. cerevisiae* and *Z. mobilis*, and (b) fermenting the feedstock to produce ethanol. In some aspects, the feedstock is inoculated with *Z. mobilis* prior to or during *S. cerevisiae* propagation. In some aspects, the feedstock is inoculated with *Z. mobilis* prior to or during fermentation. Fermentations carried out with a yeast and *Z. mobilis* co-culture can exhibit decreased levels of lactic acid bacteria by at least about 5% relative to a fermentation in the absence of *Z. mobilis*. Fermentations carried out with a yeast and *Z. mobilis* co-culture result in little or no fusel oils in the fermentation solids. Fermentations carried out with a yeast and *Z. mobilis* co-culture can exhibit decreased glycerol content in the fermentation solids relative to a fermentation in the absence of *Z. mobilis*. In some aspects, ethanol yield is increased relative to a fermentation in the absence of *Z. mobilis*. In some aspects, yeast numbers are decreased after fermentation relative to a fermentation in the absence of *Z. mobilis*.

*Z. mobilis* has a faster growth rate compared to yeast and, therefore, when inoculated at sufficient levels, is able to compete and outgrow the contaminant bacteria. *Z. mobilis* can produce ethanol in a mixed culture with yeast cells in high-salt environment, and the present disclosure utilizes *Z. mobilis* as a "probiotic" to combat bacterial infection during ethanol production by *Saccharomyces cerevisiae* (*S. cerevisiae*).

In some embodiments provided herein, *Z. mobilis* crowds out the contaminant bacteria because of its faster growth rate.

In other embodiments, an engineered *L. casei* is substituted for *Z. mobilis* in the above embodiments.

In other embodiments, a desirable aeration sensitive or oxygen sensitive bacteria, engineered or otherwise, is substituted for *Z. mobilis* in the above embodiments.

BRIEF DESCRIPTION OF THE DRAWINGS

FIG. 1 illustrates relative yeast and bacteria populations after runs varying aeration timing and inoculation timing to facilitate either aerobic or anaerobic growth.

DESCRIPTION

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

Industrial fermentation involves the breakdown of a feedstock by one or more microorganisms, e.g. yeast and/or bacteria, into one or more products. In addition to the feedstock, other nutrients may be provided to the organism to facilitate the fermentation. For example, a traditional ethanol fermentation process utilizes grain-based feedstocks (e.g., corn, sorghum/milo, barley, wheat, etc.), or other sugar sources (e.g., sugar cane, sugar beets, etc.). Enzymes, whether endogenous to the grain, added to the fermenter, or produced by yeast, convert components of the feedstock into simple sugars. Yeast, acting subsequent to or simultaneously with the enzymes, convert the simple sugars to ethanol and carbon dioxide.

In a typical ethanol production plant, corn, or other suitable primary feedstock is ground for fermentation. The entire corn kernel can be ground for fermentation, or the corn kernel may be fractionated into its component parts, and only the starchy endosperm used in fermentation. Any suitable feedstock, subjected to virtually any suitable pretreatment, can be used in the methods and compositions provided herein.

The ground corn or other primary feedstock may be combined with water to form a slurry, and the pH of the slurry mixture may be adjusted as needed. A microorganism, for example, a yeast such as *S. cerevisiae*, is added. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. Under aerobic conditions, yeast preferentially reproduces rather than producing ethanol. Under anaerobic conditions, yeast preferentially produces ethanol rather than reproducing. It is beneficial to propagate yeast under aerobic conditions to favor reproduction and build yeast cell volume and robustness. The propagated yeast may then be added to a fermenter. Other desired components can be added to the fermenter, including certain enzymes which produce monomeric sugars from polymeric sugars (e.g. glucose from starch) in the fermentable solids as in simultaneous saccharification and fermentation (SSF). These enzymes can be commercially sourced, may be present in the feedstock (genetically modified corn, for example), or may be expressed by the yeast or another microorganism co-cultured with the yeast. Exemplary enzymes include glucoamylase and alpha-amylase. Alternatively, saccharification can be performed separate from fermentation.

The slurry can be held at specified temperatures to facilitate the production of ethanol for a determined period of time. Fermenting can include contacting a mixture including sugars from the reduced plant material (e.g., fractionated plant material) with yeast under conditions suitable for growth of the yeast and production of ethanol. During fermentation, the yeast converts the sugars (e.g. glucose) to ethanol and carbon dioxide, and between the enzymatic production of sugars (e.g. glucose) and the fermentation process, sugars (e.g. glucose) may be maintained in the system at a low steady state. After fermentation, further treatment and/or distillation is performed to recover the ethanol, oil, carbon dioxide, dried distiller's grains (DDG), and/or other co-products.

Addition of an oxygen inhibited bacteria such as *Z. mobilis* and/or *L. casei* to propagation and/or fermentation can be beneficial to ethanol production. However, co-culturing such bacteria with *S. cerevisiae* is problematic as aerobic environments are conducive for rapid yeast propagation but detrimental for bacteria growth.

Provided herein are methods to facilitate co-culture of oxygen inhibited microorganism, e.g. bacteria such as *Z. mobilis* and/or *L. casei*, with an oxygen stimulated microorganism, e.g. yeast such as *S. cerevisiae*, given that the organisms have different environmental requirements. In some aspects, growth conditions favor one organism versus the other to change the ratio of microorganisms, e.g. bacteria to *S. cerevisiae*, (more, less, even) or to maintain or produce, e.g. a starting (seed), ratio during propagation or fermentation.

In order to increase ethanol concentrations in a fermentation, native LAB that convert carbohydrates to organic acid must be reduced. In addition, the fermentation can be carried out with a beneficial bacteria that produces ethanol from available carbon sources in the media. In general, beneficial bacteria which can be engineered to co-ferment with yeast include mesophilic bacteria that can ferment between 3.0-5.5 pH as the biological "chassis" or starting point of engineering, e.g. *L. paracasei*, *L. fermentum*, and *Pediococcus* species. Exemplary yeasts useful in co-fermenting with *S. cerevisiae* include *Candida* and *Pichia* species.

Besides reducing LAB, the methods described herein are useful in reducing other wild-type detrimental bacteria including other *Lactobacillus* sp., as well as *Lactococcus* sp., *Pediococcus* sp., and Weissella sp.

In some embodiments the oxygen levels within a culture vessel, e.g. a co-culture vessel, is selectively varied over time to favor the propagation of one microorganism over another to maintain or produce a desired ratio of microorganisms. In some embodiments, a culture vessel is aerated, e.g. with oxygen, air, or another oxygen containing mixture, and the aeration rate is selectively varied over time to favor the propagation of one microorganism over another. In some embodiments, a first aeration rate may be selected to favor a first microorganism during a first time period and a second aeration rate may be selected to favor a second microorganism during a second time. In some embodiments, the aeration rate may be able to be adjusted continuously between the first and second aeration rates. In some embodiments, the aeration rate may be controlled by timing of on and off periods of the aeration equipment.

In some embodiments, the aeration rate can be greater than about 0.05 vvm, for example, about 0.10 vvm, about 0.15 vvm, about 0.2 vvm, about 0.3 vvm, about 0.4 vvm, about 0.5 vvm, about 0.6 vvm, about 0.7 vvm, about 0.8 vvm, or more.

In some embodiments, the culture of one microorganism may be favored relative to another microorganism by timing the introduction of the microorganisms into the culture vessel. In some embodiments a first microorganism is introduced into a vessel while oxygen levels in the vessel and/or culture media is high and a second microorganism is introduced into the vessel when the oxygen levels have been depleted or decreased. For example, *S. cerevisiae* can be inoculated when the oxygen levels are high; *Z. mobilis* or *L. casei* can be inoculated when oxygen levels are depleted.

In some embodiments, the culture of one microorganism may be favored relative to another microorganism by selectively varying the temperature and/or pH over time to favor the propagation of one microorganism over the other.

In some embodiments, levels of aeration, timing of aeration, and timing of bacteria and yeast introduction are adjusted to balance growth of both organisms.

In some embodiments, the culture is grown by alternating sparging of an oxygen containing gas or gas mixture, e.g. air, to increase dissolved oxygen, with sparging of an inert gas like nitrogen, or adding an oxygen scavenging chemical, to decrease dissolved oxygen. For example, sparging with an oxygen containing gas or gas mixture creates oxygen containing bubbles within the culture media. The oxygen in the bubbles and the oxygen in the culture media will tend to equilibrate thus raising the oxygen content of the culture medium. Conversely, sparging with a gas having an oxygen concentration lower than the culture media, e.g. an inert gas, will decrease the oxygen in the culture media as the bubbles will draw oxygen from the culture media as they equilibrate with the culture media. A chemical oxygen scavenger would be a chemical that reacts with oxygen in the culture media to remove dissolved oxygen from the media. For example, sodium sulfite may be added to react with the oxygen to form sodium sulfate. Other examples of chemical oxygen scavengers include: other sulfites (e.g., potassium sulfite), tannins, and ascorbic acid. In some aspects, the culture could start with the yeast and the system could be sparged with air, or the culture could start with the bacteria and be sparged with the inert gas or treated with the oxygen scavenging chemical.

Timing aeration or varying aeration rate can lead to a "soft" shift in conditions favoring growth of one organism over the other as the oxygen levels of the media change relatively slowly in response to the timing or rate change. Alternatively, alternating sparging of an oxygen containing gas, e.g. air, and a low oxygen gas, e.g. nitrogen, or the use of a chemical oxygen scavenger can lead to a "hard" shift in conditions as the oxygen levels of the media change relatively quickly in response to the inert gas sparging or oxygen scavenger.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1

Co-cultures of oxygen inhibited bacteria, Z. mobilis, and oxygen stimulated yeast, S. cerevisiae, were grown in a single vessel while controlling aeration rate, controlling aeration timing, and modulating inoculation timing (for example, inoculating bacteria two hours before adding yeast) to facilitate either aerobic or anaerobic growth. Experiments were run at pilot scale to achieve scalable results. The populations of Z. mobilis, lactic acid bacteria, and S. cerevisiae were measured. The yeast cells were measured using a fluorescent dye staining technique. The bacterial cells were measured using plating methods. The fermenter was a 600 liter capacity agitated pressure vessel with an open pipe air sparger. The culture media was corn mash from a commercial ethanol plant. The mash included corn flour, sulfuric acid, backset and makeup waters. Since the mash was sourced from a production vessel, it also included a representative load of contaminating lactic acid bacteria. This contamination load was in the range of 2-8×10$^5$ CFU/ml at time zero. The fermenter was filled with 500 liters of culture media. The inoculations comprised 1×10$^7$ CFU/ml Z. mobilis from samples produced by 1 liter laboratory flask incubation of a cryo-preserved culture and 1×10$^7$ CFU/ml S. cerevisiae obtained as active dry yeast. The fermenter was fitted with an agitator comprised of a 0.75 hp motor connected by a shaft to two 45° pitched blade impellers, with a maximum impeller rotation rate of 245 RPM at 100% speed.

Table 1 provides the co-culture variables and FIG. 1 shows the results from the runs with varying conditions of aeration and timing of yeast and bacteria introduction. The aeration rate unit, vvm, is a ratio of vapor volume to liquid volume per minute. As can be seen in FIG. 1, conditions with severe yeast inhibition are shown in runs 21 and 29; conditions with mild yeast inhibition are shown in runs 18, 20, and 22; conditions that suppress Zymomonas growth are shown in run 16; conditions that promote Zymomonas growth are shown in runs 18, 20, 21, 22, 28, and 29; conditions that limit native lactic acid bacteria are shown in runs 16, 18, and 28; conditions that promote native lactic acid bacteria are shown in runs 19, 21, 22, 25, 26, and 29; conditions that grew Zymomonas but did not promote native LAB or severely inhibit yeast are shown in runs 18, 20, and 28. Yeast count data are missing from run 18; LAB count data are missing from runs 24 and 27.

TABLE 1

| | | | | |
|---|---|---|---|---|
| Run Conditions for Co-Culture | | | | |
| Run # | Yeast Pitch (hrs) | Zymo Pitch (hrs) | Aeration Rate (vvm) | Agitation rate (% of Max RPM) |
| 16 | 2 | 0 | 0.11 | 40 |
| 17 | | | ND | |
| 18 | 0 | 2 | 0.11 | 40 |
| 19 | 0 | no zymo | 0 | 40 |
| 20 | 2 | 0 | 0 | 40 |
| 21 | 4 | 0 | 0 | 40 |
| 22 | 0 | 2 | 0 | 50 |
| 23 | 4 | 0 | 1.19 | 100 |
| 24 | 0 | no zymo | 0-6 hrs: 1.19 vvm<br>6-16 hrs: 0.0 vvm | 0-6 hrs 100%<br>6-16 hrs 50% |
| 25 | 0 | 0 | 0-6 hrs: 1.19 vvm<br>6-16 hrs 0.0 vvm | 0-6 hrs 100%<br>6-16 hrs 50% |
| 26 | 0 | 6 | 0-6 hrs: 1.19 vvm<br>6-16 hrs 0.0 vvm | 0-6 hrs 100%<br>6-16 hrs 50% |
| 27 | 0 | no zymo | 0-6 hrs: 0.0 vvm<br>6-16 hrs 1.19 vvm | 0-6 hrs 0%<br>6-16 hrs 100% |
| 28 | 0 | 0 | 0-6 hrs: 0.0 vvm<br>6-16 hrs 1.19 vvm | 0-6 hrs 0%<br>6-16 hrs 100% |
| 29 | 6 | 0 | 0-6 hrs: 0.0 vvm<br>6-16 hrs 1.19 vvm | 0-6 hrs 0%<br>6-16 hrs 100% |

What is claimed is:

1. A method of producing a bioproduct comprising: inoculating a first feedstock selected from a grain-based feedstock, sugar cane, sugar beets, other carbohydrate containing streams, and combinations thereof, with yeast at least about 1 to 5 hours prior to inoculation with a bacteria selected from the group consisting of *Escherichia coli* (*E. coli*), *Zymomonas mobilis* (*Z. mobilis*), and *Lactobacillus casei* (*L. casei*) to form a co-culture, and culturing the co-culture to produce bioproduct from the first feedstock.

2. The method of claim 1, wherein the bacteria is *E. coli*.

3. The method of claim 1, wherein the bacteria is *Z. mobilis*.

4. The method of claim 1, wherein the bacteria is *L. casei*.

5. The method of claim 1, wherein the fermentation is performed with an aeration rate of about 0.05 liters of vapor volume to liquid volume per minute (vvm).

6. A method of producing a bioproduct comprising: inoculating a first feedstock selected from a grain-based feedstock, sugar cane, sugar beets, other carbohydrate containing streams, and combinations thereof, with a bacteria at least about 1 to 5 hours prior to inoculation with yeast to form a co-culture, and culturing the co-culture to produce bioproduct from the first feedstock, wherein the bacteria is selected from the group consisting of *Escherichia coli* (*E. coli*), *Zymomonas mobilis* (*Z. mobilis*), and *Lactobacillus casei* (*L. casei*) and dissolved oxygen present in the first feedstock is reduced prior to inoculation with bacteria.

7. The method of claim 6, wherein the bacteria is *E. coli*.

8. The method of claim 6, wherein the bacteria is *Z. mobilis*.

9. The method of claim 6, wherein the bacteria is *L. casei*.

10. A method of producing a bioproduct comprising: inoculating a first feedstock selected from a grain-based feedstock, sugar cane, sugar beets, other carbohydrate containing streams, and combinations thereof, with a bacteria and a yeast to form a co-culture, initially culturing the co-culture in the absence of added oxygen, then oxygenating the co-culture, and further culturing the oxygenated co-culture to produce bioproduct from the first feedstock, wherein the bacteria is selected from the group consisting of *Escherichia coli* (*E. coli*), *Zymomonas mobilis* (*Z. mobilis*), and *Lactobacillus casei* (*L. casei*).

11. The method of claim 10, wherein the bacteria is *E. coli*.

12. The method of claim 10, wherein the bacteria is *Z. mobilis*.

13. The method of claim 10, wherein the bacteria is *L. casei*.

14. The method of claim 10, wherein the step of oxygenating is performed via aerating with an oxygen-containing gas or gas mixture, injecting oxygen, or adding oxidizing chemicals.

15. The method of claim 10, wherein the step of oxygenating comprises aerating at a rate of about 0.85 liters of vapor volume to liquid volume per minute (vvm).

16. A method of producing a bioproduct comprising: inoculating a first feedstock selected from a grain-based feedstock, sugar cane, sugar beets, other carbohydrate containing streams, and combinations thereof, with a bacteria and a yeast to form a co-culture, initially culturing the co-culture under oxygenation for at least 1 hour, then culturing the co-culture in the absence of oxygenation for several hours to produce bioproduct from the first feedstock, wherein the bacteria is selected from the group consisting of *E. coli*, *Z. mobilis*, and *L. casei*.

17. The method of claim 16, wherein the bacteria is *E. coli*.

18. The method of claim 16, wherein the bacteria is *Z. mobilis*.

19. The method of claim 16, wherein the bacteria is *L. casei*.

20. The method of claim 16, wherein the step of oxygenating is performed for about 2 to about 24 hours.

21. The method of claim 16, wherein the step of oxygenating comprises aerating at a rate of about 0.85 liters of vapor volume to liquid volume per minute (vvm).

22. The method of claim 6, wherein the dissolved oxygen present in the first feedstock is reduced using an oxygen scavenger.

23. The method of claim 22, wherein the oxygen scavenger is a chemical oxygen scavenger.

24. The method of claim 23, wherein the chemical oxygen scavenger is a tannin or a sulfite.

25. The method of claim 23, wherein the chemical oxygen scavenger is selected from the group consisting of sodium sulfite, potassium sulfite, and ascorbic acid.

26. The method of claim 6, wherein the dissolved oxygen present in the first feedstock is reduced via sparging with an inert gas.

27. The method of claim 6, wherein the dissolved oxygen present in the first feedstock is reduced via sparging with a gas having an oxygen concentration lower than the culture media.

28. The method of claim 6, wherein the dissolved oxygen present in the first feedstock is reduced via sparging with nitrogen.

29. The method of claim 14, wherein the step of oxygenating is performed via aerating with an oxygen-containing gas or gas mixture for about 5 to about 20 hours.

30. The method of claim 1, wherein culturing the co-culture to produce bioproduct comprises inoculating a second feedstock selected from a grain-based feedstock, sugar cane, sugar beets, other carbohydrate containing streams, and combinations thereof, with the co-culture and culturing the co-culture in the second feedstock to produce bioproduct from the second feedstock, wherein the composition of the first and second feedstocks may be the same or different.

31. The method of claim 1, wherein the bioproduct comprises ethanol.

32. The method of claim 6, wherein culturing the co-culture to produce bioproduct further comprises inoculating a second feedstock selected from a grain-based feedstock, sugar cane, sugar beets, other carbohydrate containing streams, and combinations thereof, with the co-culture and culturing the co-culture in the second feedstock to produce bioproduct from the second feedstock, wherein the composition of the first and second feedstocks may be the same or different.

33. The method of claim 6, wherein the bioproduct comprises ethanol.

34. The method of claim 10, wherein culturing the co-culture to produce bioproduct further comprises inoculating a second feedstock selected from a grain-based feedstock, sugar cane, sugar beets, other carbohydrate containing streams, and combinations thereof, with the co-culture and culturing the co-culture in the second feedstock to produce bioproduct from the second feedstock, wherein the composition of the first and second feedstocks may be the same or different.

35. The method of claim 16, wherein culturing the co-culture to produce bioproduct further comprises inoculating a second feedstock selected from a grain-based feedstock, sugar cane, sugar beets, other carbohydrate containing streams, and combinations thereof, with the co-culture and culturing the co-culture in the second feedstock to produce ethanol, wherein the composition of the first and second feedstocks may be the same or different.

36. The method of claim 16, wherein the bioproduct comprises ethanol.

* * * * *